(12) United States Patent
Bernardo

(10) Patent No.: US 11,331,309 B2
(45) Date of Patent: May 17, 2022

(54) METHODS AND COMPOSITIONS FOR IMPROVING SLEEP

(71) Applicant: CURE Pharmaceutical Holding Corp., Oxnard, CA (US)

(72) Inventor: Jose Bernardo, Oxnard, CA (US)

( * ) Notice: Subject to any disclaimer, the term of this patent is extended or adjusted under 35 U.S.C. 154(b) by 92 days.

(21) Appl. No.: 16/432,443

(22) Filed: Jun. 5, 2019

(65) Prior Publication Data

US 2020/0383962 A1 Dec. 10, 2020

(51) Int. Cl.
| | |
|---|---|
| *A61K 31/4415* | (2006.01) |
| *A61K 31/198* | (2006.01) |
| *A61K 31/4045* | (2006.01) |
| *A61K 47/44* | (2017.01) |
| *A61K 31/015* | (2006.01) |
| *A61K 47/38* | (2006.01) |
| *A61K 47/10* | (2017.01) |
| *A61K 47/26* | (2006.01) |
| *A61K 9/00* | (2006.01) |

(52) U.S. Cl.
CPC ........... *A61K 31/4415* (2013.01); *A61K 9/006* (2013.01); *A61K 31/015* (2013.01); *A61K 31/198* (2013.01); *A61K 31/4045* (2013.01); *A61K 47/10* (2013.01); *A61K 47/26* (2013.01); *A61K 47/38* (2013.01); *A61K 47/44* (2013.01)

(58) Field of Classification Search
CPC .................................................. A61K 31/4415
See application file for complete search history.

(56) References Cited

U.S. PATENT DOCUMENTS

| | | | |
|---|---|---|---|
| 9,833,408 B1 * | 12/2017 | Greenspoon | A61K 9/0058 |
| 2019/0000907 A1 * | 1/2019 | Cohen | A23L 33/175 |
| 2020/0101009 A1 * | 4/2020 | Schobel | A61P 25/08 |

* cited by examiner

*Primary Examiner* — Yong S. Chong

(57) ABSTRACT

Compositions suitable for oral use (e.g., oral thin film) containing various excipients and a combination of melatonin, caryophyllene, GABA, L-theanine, and vitamin $B_6$. Methods of using the composition, e.g., in the treatment of a sleeping disorder, as well as methods of manufacturing the composition are also included.

22 Claims, 1 Drawing Sheet

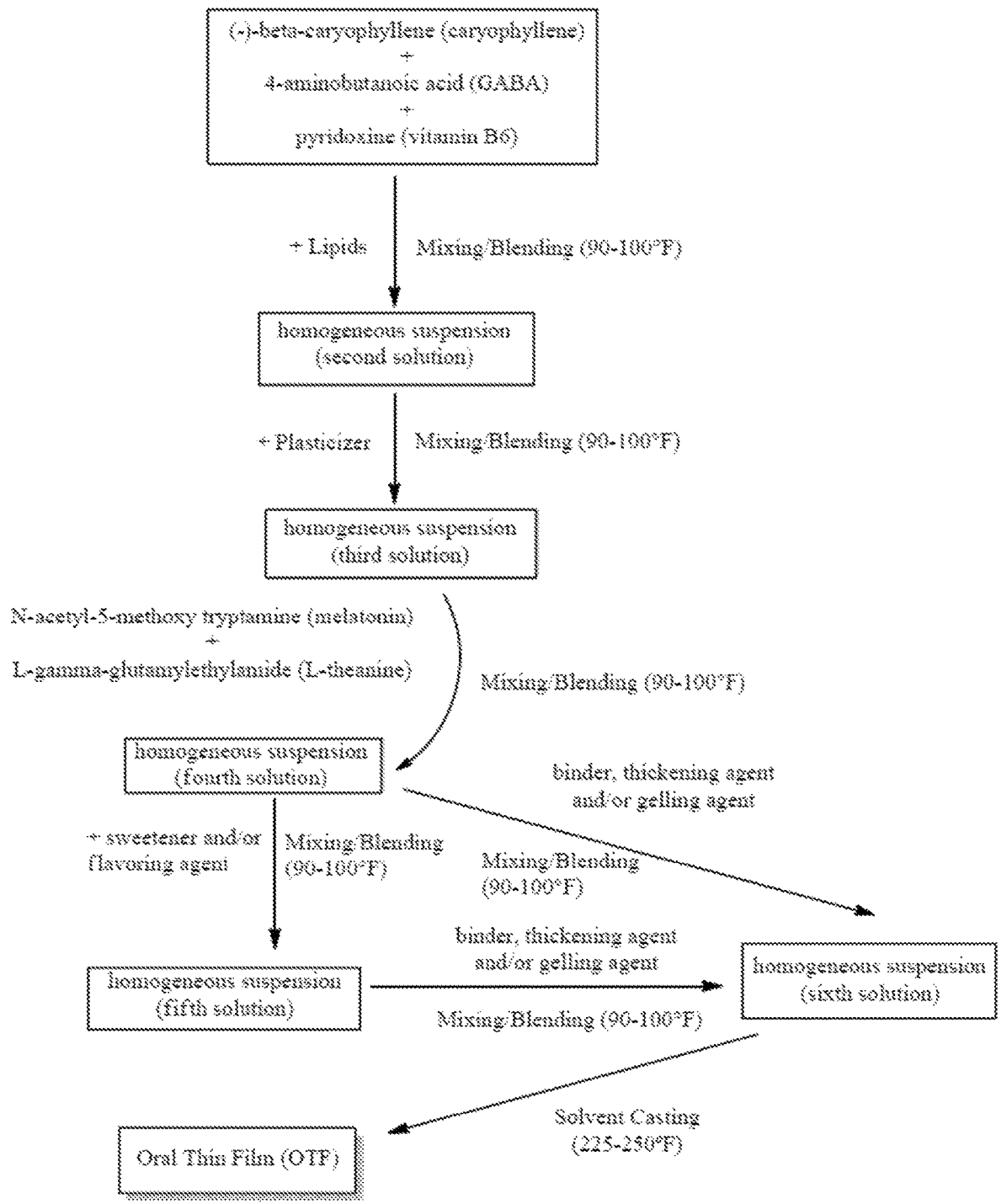

METHODS AND COMPOSITIONS FOR IMPROVING SLEEP

BACKGROUND

A sleep disorder, or somnipathy, is a medical disorder of the sleep patterns of a person or animal. Some sleep disorders are serious enough to interfere with normal physical, mental, social and emotional functioning.

Sleep disorders are broadly classified into dyssomnias, parasomnias, circadian rhythm sleep disorders involving the timing of sleep, and other disorders including ones caused by medical or psychological conditions and sleeping sickness.

Some common sleep disorders include sleep apnea (stops in breathing during sleep), narcolepsy and hypersomnia (excessive sleepiness at inappropriate times), cataplexy (sudden and transient loss of muscle tone while awake), and sleeping sickness (disruption of sleep cycle due to infection). Other disorders include sleepwalking, night terrors and bed wetting.

Thus there is a need for an improved method for reducing, treating or preventing forms of sleep disorder.

SUMMARY

The present invention provides for a composition that includes: (i) N-acetyl-5-methoxy tryptamine (melatonin), (ii) (−)-β-caryophyllene (caryophyllene), (iii) 4-aminobutanoic acid (GABA), (iv) L-γ-glutamylethylamide (L-theanine), (v) pyridoxine (vitamin B6), (vi) at least one of a binder, thickening agent, and gelling agent, (vii) plasticizer, (viii) lipid, (iv) optionally a flavoring agent, and (v) optionally a sweetener.

The present invention provides for a dietary supplement that includes: (i) N-acetyl-5-methoxy tryptamine (melatonin), (ii) (−)-β-caryophyllene (caryophyllene), (iii) 4-aminobutanoic acid (GABA), (iv) L-γ-glutamylethylamide (L-theanine), (v) pyridoxine (vitamin B6), (vi) at least one of a binder, thickening agent, and gelling agent, (vii) plasticizer, (viii) lipid, (iv) optionally a flavoring agent, and (v) optionally a sweetener.

The present invention also provides for an oral thin film (OTF) having a mass of about 110-130 mg, the OTF including: (i) about 1.35 mg to about 5 mg N-acetyl-5-methoxy tryptamine (melatonin), (ii) about 15 mg to about 25 mg (−)-β-caryophyllene (caryophyllene), (iii) about 5 mg to about 15 mg 4-aminobutanoic acid (GABA), (iv) about 5 mg to about 20 mg L-γ-glutamylethylamide (L-theanine), (v) about 2 mg to about 6 mg pyridoxine (vitamin B6), (vi) about 10 mg to about 50 mg in the aggregate of at least one of a binder, thickening agent, and gelling agent, (vii) about 5 mg to about 50 mg plasticizer, (viii) about 2 mg to about 20 mg lipid, (iv) about 2 to about 15 mg flavoring agent, and (v) about 5 mg to about 20 mg sweetener.

The present invention also provides for an oral thin film (OTF) having a mass of about 110-130 mg, the OTF including: (i) about 1.5±0.5 mg N-acetyl-5-methoxy tryptamine (melatonin), (ii) about 15±5 mg (−)-β-caryophyllene (caryophyllene), (iii) about 7.5±3 mg 4-aminobutanoic acid (GABA), (iv) about 12±6 mg L-γ-glutamylethylamide (L-theanine), (v) about 3±2 mg pyridoxine (vitamin B6), (vi) about 29±15 mg in the aggregate of at least one of binder, thickening agent, and gelling agent, (vii) about 10±4 mg plasticizer, (viii) about 2±1 mg lipid, (ix) about 8±5 mg flavoring agent, and (x) about 8±5 mg sweetener.

The present invention also provides for an oral thin film (OTF) having a mass of about 110-130 mg, the OTF including: (i) about 1.5 mg N-acetyl-5-methoxy tryptamine (melatonin), (ii) about 15 mg (−)-β-caryophyllene (caryophyllene), (iii) about 7.5 mg 4-aminobutanoic acid (GABA), (iv) about 12 mg L-γ-glutamylethylamide (L-theanine), (v) about 3.0 mg pyridoxine (vitamin B6), (vi) about 29 mg of combination of pectin and microcrystalline cellulose, (vii) about 10 mg glycerin, (viii) about 2 mg soy lecithin, (ix) about 8 mg flavoring agents, and (x) about 8 mg of a combination of sucralose and acesulfame potassium.

The present invention also provides for an oral thin film (OTF) having a mass of about 110-130 mg, the oral thin film comprising: (i) 1.5±0.5 mg N-acetyl-5-methoxy tryptamine (melatonin), (ii) 15±5 mg (−)-β-caryophyllene (caryophyllene), (iii) 7.5±3 mg 4-aminobutanoic acid (GABA), (iv) 12±6 mg L-γ-glutamylethylamide (L-theanine), (v) 3±2 mg pyridoxine (vitamin B6), (vi) 29±15 mg in the aggregate of at least one of binder, thickening agent, and gelling agent, (vii) 10±4 mg plasticizer, (viii) 2±1 mg lipid, (ix) 8±5 mg flavoring agent, and (x) 8±5 mg sweetener.

The present invention also provides for an oral thin film (OTF) comprising: (i) N-acetyl-5-methoxy tryptamine (melatonin), (ii) (−)-β-caryophyllene (caryophyllene), (iii) 4-aminobutanoic acid (GABA), (iv) L-γ-glutamylethylamide (L-theanine), (v) pyridoxine (vitamin B6), (vi) pectin, (vii) glycerin, (viii) water, (ix) natural flavors, (x) microcrystalline cellulose, (xi) sucralose, (xii) acesulfame potassium, (xiii) lecithin (soy), and (xiv) doeodorized cocoa butter.

The present invention also provides for a method of manufacturing an oral thin film (OTF). The method includes: (a) contacting (−)-β-caryophyllene (caryophyllene), 4-aminobutanoic acid (GABA), and pyridoxine (vitamin $B_6$) to provide a first solution, (b) contacting the first solution and lipids to provide a second solution, (c) contacting the second solution and plasticizer to provide a third solution, (d) contacting the third solution, N-acetyl-5-methoxy tryptamine (melatonin), and L-γ-glutamylethylamide (L-theanine) to provide a fourth solution, (e) either (1) or (2): (1) contacting the fourth solution and (i) sweetener, (ii) flavoring agent, (iii) combination of sweetener and flavoring agent, (iv) first sweetener and then flavoring agent, or (v) first flavoring agent and then sweetener, to form a fifth solution, and contacting the fifth solution and at least one of binder, thickening agent, and gelling agent, from order of lowest viscosity to highest viscosity, to provide a sixth solution, (2) contacting the fourth solution and at least one of binder, thickening agent, and gelling agent from order of lowest viscosity to highest viscosity, to provide a sixth solution, and (f) placing on a substrate and solvent casting the sixth solution.

The present invention also provides for a method that includes orally administering the inventive composition described herein, to a human, as a dietary supplement. The inventive composition is intended to supplement the diet and provide nutrients to the subject, such as vitamins (e.g., vitamin B6), hormones (e.g., melatonin), non-alpha amino acids (e.g., GABA), amino acid analogues (e.g., L-theanine), minerals, fiber, fatty acids, or amino acids that may be missing or may not be consumed in sufficient quantities in the subject's diet.

The present invention also provides for a method that includes orally administering the inventive composition described herein, to a human, to treat a condition ameliorated by any one or more of the substances of the inventive composition. The administration is carried out in an amount and for a period of time effective to treat the condition.

In specific embodiments, advantages of the invention provide for methods and compositions for improving sleep, wherein there is a relatively quick onset of action. In further specific embodiments, advantages of the invention provide for methods and compositions for improving sleep, wherein the onset of action is within about 60 minutes, within about 45 minutes, or within about 30 minutes.

In specific embodiments, advantages of the invention provide for methods and compositions (e.g., oral thin film (OTFs)) for improving sleep, wherein there is a relatively low residence time with the OTF (i.e., the time it takes for the OTF to completely dissolve when placed in the mouth). In further specific embodiments, advantages of the invention provide for methods and OTFs for improving sleep, wherein the residence time of the OTF is within about 120 seconds or within about 90 seconds. In yet further specific embodiments, advantages of the invention provide for methods and OTFs for improving sleep, wherein the residence time of the OTF is within about 60 seconds, within about 45 seconds, or within about 30 seconds.

In specific embodiments, advantages of the invention provide for methods and compositions for improving sleep wherein the improved sleep is achieved by: (i) effectively treating a sleeping disorder (somnipathy), (ii) effectively treating dyssomnias, and/or (iii) effectively treating insomnia.

In specific embodiments, advantages of the invention provide for effectively treating a sleeping disorder (somnipathy) characterized by: (i) difficulty getting to sleep, (ii) difficulty remaining asleep, (iii) poor sleep quality, (iv) decreasing sleepiness upon awakening, (v) non REM sleep, and/or (vi) preventing early awakenings.

In specific embodiments, advantages of the invention provide for treating a sleeping disorder (somnipathy) by effectively: (i) decreasing sleep onset latency, (ii) increasing total time slept, (iii) increasing overall sleep quality, (iv) decreasing sleepiness upon awakening, (v) promoting a deep sleep, (vi) promoting REM sleep, and/or (vii) preventing early awakenings.

In specific embodiments, advantages of the invention provide for methods and compositions for the effective short-term treatment of insomnia characterized by difficulties with sleep initiation.

In specific embodiments, advantages of the invention provide for methods and compositions for the effective short-term treatment of insomnia characterized by difficulties with sleep initiation and excessive sleepiness upon awakening.

In specific embodiments, advantages of the invention provide for methods of manufacturing in which a composition (e.g., oral thin film) is obtained, having the requisite homogeneity and favorable taste. In further specific embodiments, advantages of the invention provide for methods of manufacturing an oral thin film in which an intermediate homogeneous suspension (or homogeneous slurry) is obtained, and the oral thin film that is ultimately obtained therefrom has a favorable taste. The use of a suspension (or slurry) that is relatively homogeneous allows for the oral thin film obtained therefrom to have a favorable taste. As described in further detail below, the methods of manufacturing described herein can yield an intermediate homogeneous suspension (or homogeneous slurry), which can immediately or directly be casted onto a substrate and can then subsequently be extruded, to yield a thin film formed by solvent casting.

BRIEF DESCRIPTION OF THE FIGURE

FIG. 1 illustrates a method of manufacturing an oral film as described herein.

DETAILED DESCRIPTION

Reference will now be made in detail to certain claims of the invention, examples of which are illustrated in the accompanying drawings. While the invention will be described in conjunction with the enumerated claims, it will be understood that they are not intended to limit those claims. On the contrary, the invention is intended to cover all alternatives, modifications, and equivalents, which can be included within the scope of the invention as defined by the claims.

References in the specification to "one embodiment," "an embodiment," "an example embodiment," and the like, indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one of ordinary skill in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

For example, the step of contacting A with B and/or C includes: (1) contacting A with B, (2) contacting A with C, (3) contacting A with the combination of B+C, (4) contacting A with B, and subsequently contacting that combination (A+B) with C. Additionally, it includes (5) contacting A with C, and subsequently contacting that combination (A+C) with B.

In the methods of manufacturing described herein, unless explicit claim language recites otherwise, the "contacting of A with B" and the "contacting of B with A" will be construed as being the same.

The term "about" as used herein can allow for a degree of variability in a value or range, for example, within 10%, within 5%, or within 1% of a stated value or of a stated limit of a range. When a range or a list of sequential values is given, unless otherwise specified any value within the range or any value between the given sequential values is also disclosed.

As used herein, "melatonin" (also known as N-acetyl-5-methoxy tryptamine), refers to a hormone that is produced by the pineal gland in animals and regulates sleep and wakefulness.

As used herein, "caryophyllene" (also known as (–)-β-caryophyllene), refers to a natural bicyclic sesquiterpene that is a constituent of many essential oils, especially clove oil, the oil from the stems and flowers of *Syzygium aromaticum* (cloves), the essential oil of *Cannabis sativa*, rosemary, and hops. The IUPAC name is (1R,4E,9S)-4,11,11-trimethyl-8-methylidenebicyclo[7.2.0]undec-4-ene.

As used herein, "GABA" (also known as gamma-aminobutyric acid and γ-aminobutyric acid) refers to the compound with the IUPAC name 4-aminobutanoic acid.

As used herein, "L-theanine" (also known as L-γ-glutamylethylamide and $N^5$-ethyl-L-glutamine) refers to an amino acid analogue of the proteinogenic amino acids L-glutamate and L-glutamine.

As used herein, "vitamin $B_6$" refers to a group of chemically similar compounds which can be interconverted in biological systems. Vitamin $B_6$ is part of the vitamin B group of essential nutrients. Vitamin $B_6$ is part of the vitamin B group of essential nutrients. Its active form is pyridoxal 5'-phosphate (pyridoxal phosphate or PLP, having the IUPAC name (4-formyl-5-hydroxy-6-methylpyridin-3-yl) methyl phosphate). In specific embodiments, the vitamin B6 can exist as pyridoxine HCl.

As used herein, "treat" or "treating" includes preventing, ameliorating, or inhibiting a condition or disorder and/or a symptom of a condition or disorder, of a human subject. The "treatment" (and variations such as "treat" or "treating") refers to clinical intervention in an attempt to alter the natural course of the individual, and can be performed either for prophylaxis or during the course of clinical pathology. Desirable effects of treatment include one or more of preventing the occurrence or recurrence of the condition or disorder, alleviation of symptoms, diminishment of any direct or indirect pathological consequences of the condition or disorder, stabilized (i.e., not worsening) state of condition or disorder, and decreasing the rate of condition or disorder progression. In certain embodiments, the composition described herein is used to: (i) prevent the occurrence or recurrence of the condition or disorder and/or (ii) alleviation of symptoms of the condition or disorder. Those individuals in need of treatment include those already with the condition or disorder or those in which reoccurrence of the condition or disorder is to be prevented.

An "effective amount" of composition described herein refers to an amount effective, at dosages and for periods of time necessary, to achieve the desired therapeutic or prophylactic result. In some embodiments, the effective amount refers to an amount of composition described herein that (i) treats the particular condition or disorder, (ii) attenuates, ameliorates or eliminates one or more symptoms of the particular condition or disorder, or (iii) prevents or delays the onset of one or more symptoms of the particular condition or disorder described herein. In some embodiments, the effective amount of the composition described herein may, in a human subject: (i) decrease sleep onset latency, (ii) increase total time slept, (iii) increase overall sleep quality, (iv) decrease sleepiness upon awakening, and/or (v) prevent early awakenings.

As used herein, "sleeping disorder," "sleep disorder" or "somnipathy" refers to a medical disorder of the sleep patterns of a person. Polysomnography and actigraphy are tests commonly ordered for some sleep disorders.

Disruptions in sleep can be caused by a variety of issues, from teeth grinding (bruxism) to night terrors. When a person suffers from difficulty falling asleep and/or staying asleep with no obvious cause, it is referred to as insomnia.

Sleep disorders are broadly classified into dyssomnias, parasomnias, circadian rhythm sleep disorders involving the timing of sleep, and other disorders including ones caused by medical or psychological conditions and sleeping sickness.

Some common sleep disorders include sleep apnea (stops in breathing during sleep), narcolepsy and hypersomnia (excessive sleepiness at inappropriate times), cataplexy (sudden and transient loss of muscle tone while awake), and sleeping sickness (disruption of sleep cycle due to infection). Other disorders include sleepwalking, night terrors and bed wetting.

As used herein, "dyssomnias" refers to a broad classification of sleeping disorders involving difficulty getting to sleep, remaining asleep, or of excessive sleepiness when awake.

Dyssomnias are primary disorders of initiating or maintaining sleep or of excessive awakened sleepiness and are characterized by a disturbance in the amount, quality, or timing of sleep.

Subjects may complain of difficulty getting to sleep or staying asleep, intermittent wakefulness during the night, early morning awakening, or combinations of any of these.

Transient episodes are usually of little significance. Stress, caffeine, physical discomfort, daytime napping, and early bedtimes are common factors.

There are over 30 recognized kinds of dyssomnias. Major groups of dyssomnias include: Intrinsic sleep disorders, Extrinsic sleep disorders, and Circadian rhythm sleep disorders, both intrinsic and extrinsic.

As used herein, "insomnia" (also known as sleeplessness) refers to a sleep disorder where people have trouble sleeping. They may have difficulty falling asleep, or staying asleep as long as desired. Insomnia is typically followed by daytime sleepiness, low energy, irritability, and a depressed mood. It may result in an increased risk of motor vehicle collisions, as well as problems focusing and learning. Insomnia can be short term, lasting for days or weeks, or long term, lasting more than a month.

REM sleep is the portion of sleep when there are rapid eye movements (REMs). It is believed that dreams occur during REM sleep. Healthy individuals typically have 3 to 5 periods of REM sleep per night. They occur at intervals of 1-2 hours and are quite variable in length. An episode of REM sleep may last 5 minutes or over an hour. About 20% of sleep is REM sleep. If one sleeps 7-8 hours a night, perhaps an hour and half of that time, 90 minutes, is REM sleep.

REM sleep is characterized by a number of other features including rapid, low-voltage brain waves detectable on the electroencephalographic (EEG) recording, irregular breathing and heart rate and involuntary muscle jerks. By contrast, NREM (non-REM) sleep is dreamless sleep. During NREM, the brain waves on the EEG are typically slow and of high voltage, the breathing and heart rate are slow and regular, the blood pressure is low, and the sleeper is relatively still. NREM sleep is divided into 4 stages of increasing depth of sleep leading to REM sleep. About 80% of sleep is NREM sleep. If one sleeps 7-8 hours a night, all but maybe an hour and a half is believed to be spent in dreamless NREM sleep.

As used herein, "sublingual," "sublingually," "sublingual delivery" or "sublingual administration" refers to the pharmacological route of administration by which substances diffuse into the blood through tissues under the tongue.

As used herein, "buccal," "buccally," "buccal delivery" or "buccal administration" refers to a topical route of administration by which substances held or applied in the buccal area (in the cheek) diffuse through the oral mucosa (tissues which line the mouth) and enter directly into the bloodstream.

Buccal and sublingual administrations may provide better bioavailability of some actives and a more rapid onset of action compared to oral administration because the medication does not pass through the digestive system and thereby avoids first pass metabolism.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

"Oral thin film," "OTF," "oral dissolving film," "oral drug strip," "oral thin film," "thin film," "orally dissolvable film strip," or "oral strip" refers to a product used to administer active ingredients via absorption in the mouth (buccally or sublingually), the stomach (gastrically), and/or via the small intestines (enterically). The OTF is edible and pharmaceutically acceptable. A film is prepared typically using hydrophilic polymers that rapidly dissolves on the tongue, palatine tissue, or buccal cavity, delivering the active ingredient to the systemic circulation via dissolution when contact with liquid is made. The OTF (or more appropriately "thin film" or "TF") can also be used to adhere to mucosal tissue (e.g., at least one of mouth, nose, eye, vagina, and rectum), thereby locally delivering the active ingredient(s). As such, it is appreciated that those of skill in the art understand that reference to a thin film for use with mucosal tissue, such as nose, eye, vagina, and rectum, as an "oral thin film" or OTF is appropriate and acceptable.

The term "film" includes thin films and sheets, in any shape, including rectangular, square, or other desired shape. The films described herein may be any desired thickness and size such that it may be placed into the oral cavity of the user. For example, the films may have a relatively thin thickness of from about 0.1 to about 10 mils, or they may have a somewhat thicker thickness of from about 10 to about 30 mils. For some films, the thickness may be even larger, i.e., greater than about 30 mils. In addition, the term "film" includes single-layer compositions as well as multi-layer compositions, such as laminated films. The composition in its dried film form can effectively maintain a relatively uniform distribution of components through the application of controlled drying of the film. For example, the film can have no more than a 20%, 10%, 5%, or 1% variance of the active ingredient, per unit area of the film.

The substances can be selected in an amount such that a desired dissolution rate can be targeted. Upon contact with mucosal tissue (including, e.g., oral mucosa) the OTF will completely dissolve within the desired period of time. The period of time will vary but in reference to the oral cavity, the period of time will typically be within about 30-300 seconds.

Dissolving films generally fall into three main classes: fast dissolving, moderate dissolving and slow dissolving. Fast dissolving films generally dissolve in about 1 second to about 60 seconds, with it typically being less than about 30 seconds. Moderate dissolving films generally dissolve in about 1 to about 30 minutes, and slow dissolving films generally dissolve in more than 30 minutes.

The thin film can be manufactured in a manner, employing the ingredients described herein, such that any one or more of the desired pharmacokinetic metrics (e.g., dose, area under the curve, peak plasma concentration, dosing intervals, time to reach peak plasma concentration, clearance, bioavailability, etc.) are achieved. For example, the thin film can be manufactured such that the thin film provides for an immediate release (IR), controlled release (CR), modified release (MR), extended release (ER), or combination thereof, of active ingredient(s). This can be advantageous in those embodiments wherein multiple active ingredients are employed, each having different chemical and/or physical properties (e.g., pharmacokinetics, absorption kinetics, stability, solubility, bioavailability, etc.). The thin films described herein therefore possess the potential to allow the development of sensitive drug targets that may otherwise not be feasible in tablet or liquid formulations.

"Solvent" refers to a substance capable of dissolving another substance (a solute), resulting in a solution. When one substance is dissolved into another, a solution is formed. This is opposed to the situation when the compounds are insoluble like sand in water. In solution, all of the ingredients are uniformly distributed at a molecular level and no residue remains. The mixing is referred to as miscibility, whereas the ability to dissolve one compound into another is known as solubility. However, in addition to mixing, both substances in the solution interact with each other. When something is dissolved, molecules of the solvent arrange themselves around molecules of the solute. Heat is involved and entropy is increased making the solution more thermodynamically stable than the solute alone. This arrangement is mediated by the respective chemical properties of the solvent and solute, such as hydrogen bonding, dipole moment and polarizability.

In particular reference to the thin films described herein, the solvent will typically dissolve, but may also suspend, the active ingredient(s) and other substances present in the OTF. During the solvent casting step, much (if not all) of the solvent can be removed. However, any solvent remaining will become an integral part of the OTF.

As used herein, "plasticizer" refers to a substance used to achieve a desired softness and flexibility. During manufacturing of the OTF, the plasticizer can be employed to improve the texture and/or flow properties of the homogeneous solution, prior to solvent casting.

Non-limiting examples of plasticizers include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

"Binder" refers to any material or substance that holds or draws other materials together to form a cohesive whole. Liquid binders are added to a dry substance in order to draw it together in such a way that it maintains a uniform consistency. The binder can also add mucoadhesion to the OTF.

Non-limiting examples of binders include starches, pregelatinized starches, gelatin, polyvinylpyrrolidone, methylcellulose, sodium carboxymethylcellulose, ethylcellulose, polyacrylamides, polyvinyloxoazolidone, and polyvinylalcohols. If desired, the film may include other additives, such as keratin, or proteins, including proteins that are useful in forming a gel, such as gelatin.

The thin film described herein can optionally further include a mucoadhesive agent. The mucoadhesive agent, when placed in the oral cavity in contact with the mucosa therein, adheres to the mucosa. The mucoadhesive agent is especially effective in transmucosal delivery of the active ingredient, as the mucoadhesive agent permits a close and extended contact of the composition with the mucosal surface by promoting adherence of the composition or drug to the mucosa, and facilitates the release of the active ingredient from the composition. The mucoadhesive agent can be a polymeric compound, such as a cellulose derivative but it may be also a natural gum, alginate, pectin, or such similar polymer. The concentration of the mucoadhesive agent in the coating, such as a powder matrix coating, may be adjusted to vary the length of time that the film adheres to the mucosa or to vary the adhesive forces generated between the film and mucosa. The mucoadhesive agent may adhere to oral mucosa or to mucosa or tissue in other parts of the body, including the mouth, nose, eyes, vagina, and rectum.

Mucoadhesive agents include, e.g., carboxymethyl cellulose, polyvinyl alcohol, polyvinyl pyrrolidone (povidone), sodium alginate, methyl cellulose, hydroxypropyl cellulose, hydroxypropyl methyl cellulose, polyethylene glycols, carbopols, polycarbophils, carboxyvinyl copolymers, propylene glycol alginate, alginic acid, methyl methacrylate copolymers, tragacanth gum, guar gum, karaya gum, ethylene vinyl acetate, dimenthylpolysiloxanes, polyoxyalkylene block copolymers, pectin, chitosan, carrageenan, xanthan gum, gellan gum, locust bean gum, and hydroxyethylmethacrylate copolymers.

"Lipid" refers to a group of naturally occurring molecules that include fats, waxes, sterols, fat-soluble vitamins (such as vitamins A, D, E, and K), monoglycerides, diglycerides, triglycerides, phospholipids, and others. "Lipid" may also refer to ethoxylated fatty alcohols such as oleth-10 and laureth-10 and mixtures of ethoxylated mono and diglycerides such as PEG-16 macadamia glycerides and PEG-10 sunflower glycerides. The compounds are hydrophobic or amphiphilic small molecules. The amphiphilic nature of some lipids allows them to form structures such as vesicles, liposomes, or membranes in an aqueous environment. Biological lipids originate entirely or in part from two distinct types of biochemical subunits or "building-blocks": ketoacyl and isoprene groups. Using this approach, lipids may be divided into eight categories: fatty acids, glycerolipids, glycerophospholipids, sphingolipids, saccharolipids, and polyketides (derived from condensation of ketoacyl subunits); and sterol lipids and prenol lipids (derived from condensation of isoprene subunits).

Although the term lipid is sometimes used as a synonym for fats, fats are a subgroup of lipids called triglycerides. Lipids also encompass molecules such as fatty acids and their derivatives (including tri-, di-, monoglycerides, and phospholipids), as well as other sterol-containing metabolites such as cholesterol.

"Flavoring agent" refers to a substance capable of providing a flavor. In addition to providing a palatable and pleasurable factor to the user, the flavoring agent can also mask undesirable flavors present in the OTF. The flavoring agent can include natural flavoring agents (e.g., extracts).

"Flavor extract" refers to a flavoring agent obtained by extracting a part of a raw material, e.g., animal or plant material, often by using a solvent such as ethanol or water. The majority of natural essences are obtained by extracting the essential oil from the blossoms, fruit, roots, etc., or the whole plants, through four techniques: expression (when the oil is very plentiful and easily obtained, as in lemon peel), absorption (generally accomplished by steeping in alcohol, as vanilla beans), maceration (used to create smaller bits of the whole, as in making peppermint extract, etc.), and distillation (used with maceration, but in many cases, it requires expert chemical knowledge and the erection of costly stills).

Flavoring agents can include breath freshening compounds like menthol, spearmint, and cinnamon, coffee beans, other flavors or fragrances such as fruit (e.g., cherry, orange, grape, etc.) flavors, especially those used for oral hygiene, as well as actives used in dental and oral cleansing such as quaternary ammonium bases. The effect of flavors may be enhanced using flavor enhancers like tartaric acid, citric acid, vanillin, or the like.

"Sweetener" refers to a substance capable of providing a palatable and pleasurable factor to the user, and/or capable of masking undesirable flavors present in the OTF. The sweetener can include one or more artificial sweeteners, one or more natural sweeteners, or a combination thereof.

Artificial sweeteners include, e.g., acesulfame and its various salts such as the potassium salt (available as Sunett®), alitame, aspartame (available as NutraSweet® and Equal®), salt of aspartame-acesulfame (available as Twinsweet®), neohesperidin dihydrochalcone, naringin dihydrochalcone, dihydrochalcone compounds, neotame, sodium cyclamate, saccharin and its various salts such as the sodium salt (available as Sweet'N Low®), *stevia*, chloro derivatives of sucrose such as sucralose (available as Kaltame® and Splenda®), and mogrosides.

Natural sweeteners include, e.g., glucose, dextrose, invert sugar, fructose, sucrose, glycyrrhizin; monoammonium glycyrrhizinate (sold under the trade name MagnaSweet®); *Stevia rebaudiana* (Stevioside), natural intensive sweeteners, such as Lo Han Kuo, polyols such as sorbitol, mannitol, xylitol, erythritol, and the like.

"Palatable" refers to a substance (e.g., oral thin film) being relatively acceptable or agreeable to the palate or taste (e.g., sweet or savory), and in some cases to the olfactory nerves. In specific embodiments, advantages of the invention include the OTF being palatable, such that it is relatively acceptable or agreeable to the palate or taste (e.g., sweet or savory) of the human subject, and in further embodiments to the olfactory nerves.

"Dye or pigment" or "coloring agent" refers to a substance that imparts coloring and/or aesthetic appearance to the OTF. A dye is a colored substance that has an affinity to the substrate to which it is being applied. The dye is generally applied in an aqueous solution, and requires a mordant to improve the fastness of the dye on the fiber. A pigment is a material that changes the color of reflected or transmitted light as the result of wavelength-selective absorption. This physical process differs from fluorescence, phosphorescence, and other forms of luminescence, in which a material emits light. Both dyes and pigments appear to be colored because they absorb some wavelengths of light more than others. In contrast with a dye, a pigment generally is insoluble, and has no affinity for the substrate. Some dyes can be precipitated with an inert salt to produce a lake pigment, and based on the salt used they could be aluminum lake, calcium lake or barium lake pigments.

One or more dyes, pigments, and coloring agents can be employed in the manufacture of the thin film, such that the thin film has the desired color. Suitable colors include, e.g., white, black, yellow, blue, green, pink, red, orange, violet, indigo, and brown. In specific embodiments, the color of the thin film can indicate the contents (e.g., one or more active and/or inactive ingredients) contained therein.

"Preservative" refers to an agent that extends the storage life of food and non-food products by retarding or preventing deterioration of flavor, odor, color, texture, appearance, nutritive value, or safety. A preservative need not provide a lethal, irreversible action resulting in partial or complete microbial cell destruction or incapacitation. Sterilants, sanitizers, disinfectants, sporicides, viracides and tuberculocidal agents provide such an irreversible mode of action, sometimes referred to as "bactericidal" action. In contrast, a preservative can provide an inhibitory or bacteriostatic action that is reversible, in that the target microbes can resume multiplication if the preservative is removed. The principal differences between a preservative and a sanitizer primarily involve mode of action (a preservative prevents growth rather than killing microorganisms) and exposure time (a preservative has days to months to act whereas a sanitizer has at most a few minutes to act).

"Tensile strength" refers to the maximum stress that a material can withstand while being stretched or pulled before failing or breaking Tensile strength is the opposite of compressive strength and the values can be quite different. Tensile strength is defined as a stress, which is measured as force per unit area. For some non-homogeneous materials (or for assembled components) it can be reported just as a force or as a force per unit width. In the SI system, the unit is the pascal (Pa) (or a multiple thereof, often megapascals (MPa), using the mega-prefix); or, equivalently to pascals, newtons per square meter (N/m2). The customary unit is pounds-force per square inch (lbf/in2 or psi), or kilo-pounds per square inch (ksi, or sometimes kpsi), which is equal to 1000 psi; kilo-pounds per square inch are commonly used for convenience when measuring tensile strengths. Typically, the testing involves taking a small sample with a fixed cross-section area, and then pulling it with a controlled, gradually increasing force until the sample changes shape or breaks. In specific embodiments, advantages of the invention include the OTF having a suitable tensile strength.

"Pliable" refers to the ability of an article to readily bend, be flexible, or to be supple. In specific embodiments, advantages of the invention include the OTF being pliable.

"Non-sticky" refers to an article (e.g., thin film) not having the property of readily adhering or sticking to another surface (e.g., another article, manufacturing equipment, packaging material, the user, etc.). In specific embodiments, advantages of the invention include the OTF being non-sticky.

"Soft" refers to an article being relatively smooth and agreeable to the touch; not rough or coarse. Such an article will be capable of producing agreeable sensations, pleasant or comfortable, upon contact with an animal such as a human. In specific embodiments, advantages of the invention include the OTF being soft.

"Chewable configuration" refers to an article being manufactured in such a manner and with ingredients, that it possesses a configuration capable of being readily chewed by an animal, such as a human. In specific embodiments, advantages of the invention include the OTF being chewable.

"Malleable configuration" refers to an article being manufactured in such a manner and with ingredients, that it possesses a configuration capable of being readily shaped or changed in form (e.g., folded, bent, rolled, twisted, flexed, etc.) without breaking. In specific embodiments, advantages of the invention include the OTF having a malleable configuration.

"Ductile property" refers to the ability of an article (e.g., thin film) being readily shaped or changed in form (e.g., folded, bent, rolled, twisted, flexed, etc.) without breaking. In specific embodiments, advantages of the invention include the OTF having a suitable ductile property.

"Mixing" refers to the act of combining, uniting, and/or joining multiple substances, into one mass, collection, or assemblage (e.g., slurry), generally with a thorough and continuous contacting of the constituents.

"Blending" refers to the act of mixing that employs equipment typically referred to as a blender, or any device capable of blending a mixture. The mixing can provide a relatively smooth mixture, where the constituents are inseparable. When used in the context of "high shear blending", the blender has sharp edged blades and is used at high speed (1000-10,000 rpm).

"Mixture" refers to the mass, collection, or assemblage (e.g., slurry) obtained from the act of mixing. Typically the mixture obtained from the mixing or blending will be a homogeneous solution.

"Cooling" refers to the act of removing or transferring a sufficient amount of energy (e.g., thermal energy), within a suitable period of time, such that a decrease in temperature is experienced.

"Slurry" refers to a relatively viscous mixture, but it flows freely.

As used herein, "contacting" refers to the act of touching, making contact, or of bringing substances into immediate proximity. Typically (unless specified otherwise), the order of contacting specified is not significant, such that contacting A with B is functionally the same as contacting B with A.

"Hot extruding" refers to the act of extruding an article, while the article is currently being heated, or was previously heated, such that the article is at an elevated temperature during the extruding process. The extruding process typically includes forcing the article through a die, thereby obtaining a desired cross-section.

"Casting" or "film casting" refers to the act of removing liquid (e.g., water and/or solvent) from a mixture (e.g., slurry), such that a film is produced.

"Condensing" refers to the act of removing liquid (e.g., water and/or solvent).

"Heating" refers to the act of applying or transferring a sufficient amount of energy (e.g., thermal energy), within a suitable period of time, such that a rise in temperature is experienced.

"Conductive heat transfer" or "conduction" refers to the transfer of heat from one condensed material into another condensed material that does not involve bulk motion within either of the condensed media.

"Radiative heat transfer" or "radiation" refers to the transfer of heat from one article to another by way of electromagnetic means, usually by infrared radiation, but can also be microwave radiation.

"Convective heat transfer" or "convection" refers to the transfer of heat from one article to another, by the movement of fluids. Convection is usually the dominant form of heat transfer in liquids and gases. Although often discussed as a distinct method of heat transfer, convective heat transfer involves the combined processes of conduction (heat diffusion) and advection (heat transfer by bulk fluid flow).

Convection can be "forced" by movement of a fluid by means other than buoyancy forces (for example, a water pump in an automobile engine). In some cases, natural buoyancy forces alone are entirely responsible for fluid motion when the fluid is heated, and this process is called "natural convection." An example is the draft in a chimney or around any fire. In natural convection, an increase in temperature produces a reduction in density, which causes fluid motion due to pressures and forces when fluids of different densities are affected by gravity (or any g-force). For example, when water is heated on a stove, hot water from the bottom of the pan rises, displacing the colder denser liquid which falls. After heating has stopped, mixing and conduction from this natural convection eventually result in a nearly homogeneous density, and even temperature.

Two types of convective heat transfer can be distinguished: free or natural convection (passive) and forced convection (active). Active convection occurs when a fluid is forced to flow over the surface by an external source such as fans, by stirring, and pumps, creating an artificially induced convection current. Passive convention occurs when fluid motion is caused by buoyancy forces that result from the density variations due to variations of temperature in the fluid. In the absence of an external source, when the fluid is in contact with a hot surface, its molecules separate and scatter, causing the fluid to be less dense. As a consequence, the fluid is displaced while the cooler fluid gets denser and the fluid sinks Thus, the hotter volume transfers heat towards the cooler volume of that fluid. Familiar examples are the upward flow of air due to a fire or hot object and the circulation of water in a pot that is heated from below.

"In vacuo" refers to under vacuum. The vacuum can be a partial vacuum or a complete vacuum. Typically, the vacuum will be a partial vacuum (e.g., a reduced pressure) such as, e.g., a pressure of less than about 30 mm mercury (Hg). Specifically, the reduced pressure can be less than about 29 mm mercury (Hg). More specifically, the reduced pressure can be about 10 to about 29 mm of mercury (Hg).

"Packaging material" refers to those materials and substances employed to package the product (e.g., thin film). Such materials are widely known to those of skill in the art.

"Enclosing" refers to the packaging materials containing or holding the product (e.g., thin film) by surrounding the product with the packaging material. The packaging materials can partially surround the product, or can completely surround the product. Typically, to ensure safety (e.g., no tampering with product) and freshness, the packaging materials will completely surround the product. For example, the packaging materials can form a relatively vapor impermeable enclosure of the product.

"Printed indicia" refers to a marking, image, text, and/or symbol located on the surface of the packaging material. The indicia can be placed on the surface of the packaging material by any suitable means (e.g., ink printing, laser printing, etc.). The indicia can include, e.g., a printed message or instructions, list of ingredients (active and inactive), weight of product, manufacturer name and address, manufacturer trademark, etc. The indicia can be placed on the surfaces of the thin film itself and can include information such as manufacturer trademark, weight of product, weight of active ingredients, manufacturer name, serial numbers, lot numbers, etc.

The thin films described herein can be perforated. "Perforated" refers to the one or more holes, apertures or scores existing along a line to facilitate separation. Perforations on the thin films allow the user to conveniently administer smaller dosages of the active ingredient. This is especially useful, for example, when the subject is a child, who should receive a smaller dosage. Accurate dosing can be metered, e.g., by the weight, size, age, etc. of the subject.

Additional/Optional Components

A variety of optional components and fillers also may be added to the films. These may include, without limitation: surfactants; anti-foaming agents, such as silicone-containing compounds, which promote a smoother film surface by releasing oxygen from the film; thermo-setting gels such as pectin, carrageenan, and gelatin, which help in maintaining the dispersion of components; and inclusion compounds, such as cyclodextrins and caged molecules. In some embodiments, more than one active ingredient may be included in the film.

Additives may be included in the films. Examples of classes of additives include lubricants, buffering agents, stabilizers, blowing agents, fillers, bulking agents, fragrances, release modifiers, adjuvants, flow accelerators, mold release agents, granulating agents, diluents, buffers, absorbents, glidants, adhesives, anti-adherents, acidulants, softeners, resins, demulcents, solvents, surfactants, emulsifiers, elastomers and mixtures thereof. Further additives include inorganic fillers, such as the oxides of magnesium aluminum, silicon, titanium, etc. These additives may be added with the active agent(s).

It further may be useful to add silicon dioxide, calcium silicate, and/or titanium dioxide in a concentration of about 0.02% to about 1% by weight of the total composition. These compounds typically act as flow agents.

Kits

Pharmaceutical kits are also within the ambit of the present invention. Such kits include a therapeutically effective amount of a thin film as described herein. Sterilization of the thin film and/or packaging material may be carried out using conventional sterilization methodology well-known to those skilled in the art. Instructions or printed indicia, either as inserts or as labels, indicating quantities of the components to be administered, guidelines for administration, may also be included in the kit.

Utility

The thin films described herein can be useful to deliver active ingredient(s) to the intended target. The thin film can be placed, e.g., in the mouth thereby administering active ingredient(s) via absorption in the mouth (transmucosally, buccally or sublingually). Such an OTF will be edible (suitable for human consumption), and pharmaceutically acceptable. The thin films can be prepared typically using hydrophilic polymers that rapidly dissolve on the tongue or buccal cavity, delivering the active ingredient to the systemic circulation via dissolution when contact with liquid is made. The thin film can also be used to adhere to mucosal tissue (e.g., mouth), thereby locally delivering the active ingredient(s) to that bodily tissue. As such, the mucoadhesive films may be used for the administration of active(s) to specific oral surfaces.

The films may be applied under or to the tongue of the mammal. When this is desired, a specific film shape such as a square or rectangle, or a shape corresponding to the shape of the tongue, may be preferred. Therefore the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

Another use for the thin films described herein takes advantage of the films' tendency to dissolve quickly when introduced to a liquid. Active ingredient(s) may be introduced to a liquid (or liquid containing substance) by preparing a film as described herein, introducing it to a liquid (or liquid containing substance), and allowing it to dissolve. This may be used either to prepare a liquid dosage form of active(s). This may also be used to flavor a beverage or food product, or to add active ingredient(s) to a beverage or food product.

Methods of Manufacturing

The present invention provides for a method of manufacturing the oral thin film (OTF) described herein. The method can be carried out in any suitable manner and under any suitable conditions, provided the oral thin film (OTF), as described herein, is obtained. In specific embodiments, the method is described below (as illustrated in FIG. 1). Specifically, the method of manufacturing the oral thin film (OTF) includes:

(a) contacting (−)-β-caryophyllene (caryophyllene), 4-aminobutanoic acid (GABA), and pyridoxine (vitamin $B_6$) to provide a first solution, (b) contacting the first solution and lipids to provide a second solution, (c) contacting the second solution and plasticizer to provide a third solution, (d) contacting the third solution, N-acetyl-5-methoxy tryptamine (melatonin), and L-γ-glutamylethylamide (L-theanine) to provide a fourth solution, (e) either (1) or (2):

(1) contacting the fourth solution and (i) sweetener, (ii) flavoring agent, (iii) combination of sweetener and flavoring agent, (iv) first sweetener and then flavoring agent, or (v) first flavoring agent and then sweetener, to form a fifth solution, and contacting the fifth solution and at least one of binder, thickening agent, and gelling agent, from order of lowest viscosity to highest viscosity, to provide a sixth solution, (2) contacting the fourth solution and at least one of binder, thickening agent, and gelling agent from order of lowest viscosity to highest viscosity, to provide a sixth solution, and (f) placing on a substrate and solvent casting the sixth solution.

In step (a), the contacting of the (−)-β-caryophyllene (caryophyllene), 4-aminobutanoic acid (GABA), and pyridoxine (vitamin $B_6$) is carried out to provide the first solution. The contacting can readily be carried in any suitable manner, to effectively provide the first solution, which is preferably a homogeneous suspension. For example, the contacting of the (−)-β-caryophyllene (caryophyllene), 4-aminobutanoic acid (GABA), and pyridoxine (vitamin $B_6$) can be carried out such that the substances are rapidly mixed or blended. Additionally, the contacting (e.g., mixing or blending) can be carried out under any suitable conditions (e.g., at about 90-100° F.) to effectively provide the first solution, which is preferably a homogeneous suspension.

In step (b), the contacting of the first solution and lipids is carried out to provide the second solution. The contacting can readily be carried in any suitable manner, to effectively provide the second solution, which is preferably a homogeneous suspension. For example, the contacting of the first solution and lipids can be carried out such that the substances are rapidly mixed or blended. Additionally, the contacting (e.g., mixing or blending) can be carried out under any suitable conditions (e.g., at about 90-100° F.) to effectively provide the second solution, which is preferably a homogeneous suspension.

In step (c), the contacting of the second solution and the plasticizer is carried out to provide the third solution. The contacting can readily be carried in any suitable manner, to effectively provide the third solution, which is preferably a homogeneous suspension. For example, the contacting of the second solution and the plasticizer can be carried out such that the substances are rapidly mixed or blended. Additionally, the contacting (e.g., mixing or blending) can be carried out under any suitable conditions (e.g., at about 90-100° F.) to effectively provide the third solution, which is preferably a homogeneous suspension.

In step (d), the contacting of third solution, N-acetyl-5-methoxy tryptamine (melatonin), and L-gamma-glutamylethylamine (L-theanine) can be carried out to provide the fourth solution. The contacting can readily be carried in any suitable manner, to effectively provide the fourth solution, which is preferably a homogeneous suspension. For example, the contacting of the third solution and the plasticizer can be carried out such that the substances are rapidly mixed or blended. Additionally, the contacting (e.g., mixing or blending) can be carried out under any suitable conditions (e.g., at about 90-100° F.) to effectively provide the fourth solution, which is preferably a homogeneous suspension.

In step (e), it is shown that the method of manufacturing the oral thin film (OTF) can optionally include a sweetener and/or flavoring agent. If the sweetener and/or flavoring agent is to be included in the oral thin film (OTF), the contacting of the fourth solution with the sweetener and/or flavoring agent can be carried out in any suitable manner, to effectively provide the fifth solution, which is preferably a homogeneous suspension. For example, the contacting of the fourth solution with the sweetener and/or flavoring agent can be carried out such that the substances are rapidly mixed or blended. Additionally, the contacting (e.g., mixing or blending) can be carried out under any suitable conditions (e.g., at about 90-100° F.) to effectively provide the fifth solution, which is preferably a homogeneous suspension.

Subsequently, the contacting of the fifth solution with the binder, thickening agent and/or gelling agent can readily be carried out to provide the sixth solution. For example, the substances can be rapidly mixed or blended. The contacting (e.g., mixing or blending) can be carried out under suitable conditions (e.g., at about 90-100° F.) to effectively provide the sixth solution, which is preferably a homogeneous suspension. For example, the contacting of the fifth solution with the binder, thickening agent and/or gelling agent can be carried out such that the substances are rapidly mixed or blended. Additionally, the contacting (e.g., mixing or blending) can be carried out under any suitable conditions (e.g., at about 90-100° F.) to effectively provide the sixth solution, which is preferably a homogeneous suspension.

Alternatively, if the sweetener and/or flavoring agent is not to be included in the oral thin film (OTF), the contacting of the fourth solution with the binder, thickening agent and/or gelling agent can readily be carried out to provide the sixth solution. For example, the substances can be rapidly mixed or blended. The contacting (e.g., mixing or blending) can be carried out under suitable conditions (e.g., at about 90-100° F.) to effectively provide the sixth solution, which is preferably a homogeneous suspension. For example, the contacting of the fourth solution with the binder, thickening agent and/or gelling agent can be carried out such that the substances are rapidly mixed or blended. Additionally, the contacting (e.g., mixing or blending) can be carried out under any suitable conditions (e.g., at about 90-100° F.) to effectively provide the sixth solution, which is preferably a homogeneous suspension.

Either way, the oral thin film can be obtained by solvent casting the sixth solution. The solvent casting can be carried out in any suitable manner (e.g., placed on a substrate, such as siliconized paper and/or polyester film), provided the oral thin film (OTF) is effectively obtained. Additionally, the solvent casting can be carried out under any suitable conditions (e.g., at a temperature of about 225-250° F.), provided the oral thin film (OTF) is effectively obtained.

Specific ranges, values, and embodiments provided below are for illustration purposes only, and do not otherwise limit the scope of the disclosed subject matter, as defined by the claims.

Specific Ranges, Values, and Embodiments

In specific embodiments, the inventive composition is in the form of an oral thin film (OTF).

In specific embodiments, the inventive composition is in the form of an oral thin film (OTF), having a mass of about 110-130 mg.

In specific embodiments, the inventive composition is in the form of an oral thin film (OTF) having the following dimensions: 44±6 mm x 22±3 mm x 0.12±0.02 mm.

In specific embodiments, the inventive composition is in the form of an oral thin film (OTF) having the following dimensions: 44±3 mm x 22±1 mm x 0.12±0.01 mm.

In specific embodiments, the inventive composition is in the form of an oral thin film (OTF) having the following dimensions: about 44 mm x about 22 mm x about 0.12 mm.

In specific embodiments, the melatonin is present in about 1 wt. % to about 5 wt. % of the composition.

In specific embodiments, the composition is formulated as a unit dosage form having a mass of about 110-130 mg and the melatonin is present in about 1.35 mg to about 5.0 mg.

In specific embodiments, the caryophyllene is present in about 10 wt. % to about 25 wt. % of the composition.

In specific embodiments, the composition is formulated as a unit dosage form having a mass of about 110-130 mg and the caryophyllene is present in about 15 mg to about 25 mg.

In specific embodiments, the GABA is present in about 3 wt. % to about 15 wt. % of the composition.

In specific embodiments, the composition is formulated as a unit dosage form having a mass of about 110-130 mg and the GABA is present in about 5 mg to about 15 mg.

In specific embodiments, the L-theanine is present in about 3 wt. % to about 20 wt. % of the composition.

In specific embodiments, the composition is formulated as a unit dosage form having a mass of about 110-130 mg and the L-theanine is present in about 5 mg to about 20 mg.

In specific embodiments, the vitamin $B_6$ is present in about 1.5 wt. % to about 5.5 wt. % of the composition.

In specific embodiments, the composition is formulated as a unit dosage form having a mass of about 110-130 mg and the vitamin $B_6$ is present in about 2 mg to about 6 mg.

In specific embodiments, the binder, thickening agent, and/or gelling agent is selected from the group consisting of pectin, carboxymethyl cellulose sodium, pullulan, carrageenan, hydroxypropyl methylcellulose, microcrystalline cellulose, xanthan gum, polyvinylpyrrolidone, and combinations thereof.

In specific embodiments, the at least one of the binder, thickening agent, and gelling agent is present in a total amount of about 10 wt. % to about 40 wt. % of the composition.

In specific embodiments, the plasticizer includes at least one of glycerol, sorbitol, propylene glycol, and polyethylene glycol.

In specific embodiments, the plasticizer is present in about 5 wt. % to about 40 wt. %. of the composition.

In specific embodiments, the lipid includes at least one of lecithin, hydroxylated lecithin, grapeseed oil, cocoa butter, shea butter, olive oil, almond oil, peanut oil, canola oil, sesame oil, hazelnut oil, and coconut oil.

In specific embodiments, the lipid is present in about 2 wt. % to about 15 wt. %. of the composition.

In specific embodiments, the flavoring agent is present and includes a natural flavoring agent.

In specific embodiments, the flavoring agent is present and includes an artificial flavoring agent.

In specific embodiments, the sweetener is present and includes at least one of sucralose, acesulfame potassium, xylitol, ammonium glycyrrhizinate and *stevia*.

In specific embodiments, with the method of manufacturing the oral thin film (OTF), in step (a), the contacting is carried out in the presence of a solvent.

In specific embodiments, with the method of manufacturing the oral thin film (OTF), in step (a), the contacting includes rapidly mixing or blending, to provide a first solution that is a homogeneous suspension.

In specific embodiments, with the method of manufacturing the oral thin film (OTF), in step (a), the contacting includes rapidly mixing or blending, at a temperature of at least about 90° F., to provide a first solution that is a homogeneous suspension.

In specific embodiments, with the method of manufacturing the oral thin film (OTF), in step (a), the contacting includes rapidly mixing or blending, at a temperature of up to about 100° F., to provide a first solution that is a homogeneous suspension.

In specific embodiments, with the method of manufacturing the oral thin film (OTF), in step (a), the contacting includes rapidly mixing or blending, at about 85-120° F., to provide a first solution that is a homogeneous suspension.

In specific embodiments, with the method of manufacturing the oral thin film (OTF), in step (a), the contacting includes rapidly mixing or blending, at about 90-100° F., to provide a first solution that is a homogeneous suspension.

In specific embodiments, with the method of manufacturing the oral thin film (OTF), in step (b), the contacting is carried out in the presence of a solvent.

In specific embodiments, with the method of manufacturing the oral thin film (OTF), in step (b), the contacting includes rapidly mixing or blending, to provide a second solution that is a homogeneous suspension.

In specific embodiments, with the method of manufacturing the oral thin film (OTF), in step (b), the contacting includes rapidly mixing or blending, at a temperature of at least about 90° F., to provide a second solution that is a homogeneous suspension.

In specific embodiments, with the method of manufacturing the oral thin film (OTF), in step (b), the contacting includes rapidly mixing or blending, at a temperature of up to about 100° F., to provide a second solution that is a homogeneous suspension.

In specific embodiments, with the method of manufacturing the oral thin film (OTF), in step (b), the contacting includes rapidly mixing or blending, at about 85-120° F., to provide a second solution that is a homogeneous suspension.

In specific embodiments, with the method of manufacturing the oral thin film (OTF), in step (b), the contacting includes rapidly mixing or blending, at about 90-100° F., to provide a second solution that is a homogeneous suspension.

In specific embodiments, with the method of manufacturing the oral thin film (OTF), in step (c), the contacting is carried out in the presence of a solvent.

In specific embodiments, with the method of manufacturing the oral thin film (OTF), in step (c), the contacting includes rapidly mixing or blending, to provide a third solution that is a homogeneous suspension.

In specific embodiments, with the method of manufacturing the oral thin film (OTF), in step (c), the contacting includes rapidly mixing or blending, at a temperature of at least about 90° F., to provide a third solution that is a homogeneous suspension.

In specific embodiments, with the method of manufacturing the oral thin film (OTF), in step (c), the contacting includes rapidly mixing or blending, at a temperature of up to about 100° F., to provide a third solution that is a homogeneous suspension.

In specific embodiments, with the method of manufacturing the oral thin film (OTF), in step (c), the contacting includes rapidly mixing or blending, at about 85-120° F., to provide a third solution that is a homogeneous suspension.

In specific embodiments, with the method of manufacturing the oral thin film (OTF), in step (c), the contacting includes rapidly mixing or blending, at about 90-100° F., to provide a third solution that is a homogeneous suspension.

In specific embodiments, with the method of manufacturing the oral thin film (OTF), in step (d), the contacting is carried out in the presence of a solvent.

In specific embodiments, with the method of manufacturing the oral thin film (OTF), in step (d), the contacting includes rapidly mixing or blending, to provide a fourth solution that is a homogeneous suspension.

In specific embodiments, with the method of manufacturing the oral thin film (OTF), in step (d), the contacting includes rapidly mixing or blending, at a temperature of at least about 90° F., to provide a fourth solution that is a homogeneous suspension.

In specific embodiments, with the method of manufacturing the oral thin film (OTF), in step (d), the contacting includes rapidly mixing or blending, at a temperature of up to about 100° F., to provide a fourth solution that is a homogeneous suspension.

In specific embodiments, with the method of manufacturing the oral thin film (OTF), in step (d), the contacting includes rapidly mixing or blending, at about 85-120° F., to provide a fourth solution that is a homogeneous suspension.

In specific embodiments, with the method of manufacturing the oral thin film (OTF), in step (d), the contacting includes rapidly mixing or blending, at about 90-100° F., to provide a fourth solution that is a homogeneous suspension.

In specific embodiments, with the method of manufacturing the oral thin film (OTF), in step (e)(1), the contacting is carried out in the presence of a solvent.

In specific embodiments, with the method of manufacturing the oral thin film (OTF), in step (e)(1), the contacting includes rapidly mixing or blending, to provide a fifth solution that is a homogeneous suspension.

In specific embodiments, with the method of manufacturing the oral thin film (OTF), in step (e)(1), the contacting includes rapidly mixing or blending, to provide a sixth solution that is a homogeneous suspension.

In specific embodiments, with the method of manufacturing the oral thin film (OTF), in step (e)(1), the contacting includes rapidly mixing or blending, at a temperature of at least about 90° F., to provide a fifth solution that is a homogeneous suspension.

In specific embodiments, with the method of manufacturing the oral thin film (OTF), in step (e)(1), the contacting includes rapidly mixing or blending, at a temperature of at least about 90° F., to provide a sixth solution that is a homogeneous suspension.

In specific embodiments, with the method of manufacturing the oral thin film (OTF), in step (e)(1), the contacting includes rapidly mixing or blending, at a temperature of up to about 100° F., to provide a fifth solution that is a homogeneous suspension.

In specific embodiments, with the method of manufacturing the oral thin film (OTF), in step (e)(1), the contacting includes rapidly mixing or blending, at a temperature of up to about 100° F., to provide a sixth solution that is a homogeneous suspension.

In specific embodiments, with the method of manufacturing the oral thin film (OTF), in step (e)(1), the contacting includes rapidly mixing or blending, at about 85-120° F., to provide a fifth solution that is a homogeneous suspension.

In specific embodiments, with the method of manufacturing the oral thin film (OTF), in step (e)(1), the contacting includes rapidly mixing or blending, at about 85-120° F., to provide a sixth solution that is a homogeneous suspension.

In specific embodiments, with the method of manufacturing the oral thin film (OTF), in step (e)(1), the contacting includes rapidly mixing or blending, at about 90-100° F., to provide a fifth solution that is a homogeneous suspension.

In specific embodiments, with the method of manufacturing the oral thin film (OTF), in step (e)(1), the contacting includes rapidly mixing or blending, at about 90-100° F., to provide a sixth solution that is a homogeneous suspension.

In specific embodiments, with the method of manufacturing the oral thin film (OTF), in step (e)(2), the contacting is carried out in the presence of a solvent.

In specific embodiments, with the method of manufacturing the oral thin film (OTF), in step (e)(2), the contacting includes rapidly mixing or blending, to provide a sixth solution that is a homogeneous suspension.

In specific embodiments, with the method of manufacturing the oral thin film (OTF), in step (e)(2), the contacting includes rapidly mixing or blending, at a temperature of at least about 90° F., to provide a sixth solution that is a homogeneous suspension.

In specific embodiments, with the method of manufacturing the oral thin film (OTF), in step (e)(2), the contacting includes rapidly mixing or blending, at a temperature of up to about 100° F., to provide a sixth solution that is a homogeneous suspension.

In specific embodiments, with the method of manufacturing the oral thin film (OTF), in step (e)(2), the contacting includes rapidly mixing or blending, at about 85-120° F., to provide a sixth solution that is a homogeneous suspension.

In specific embodiments, with the method of manufacturing the oral thin film (OTF), in step (e)(2), the contacting includes rapidly mixing or blending, at about 90-100° F., to provide a sixth solution that is a homogeneous suspension.

In specific embodiments, with the method of manufacturing the oral thin film (OTF), in step (f), the substrate includes at least one of siliconized paper and polyester film.

In specific embodiments, with the method of manufacturing the oral thin film (OTF), in step (f), the substrate includes siliconized paper.

In specific embodiments, with the method of manufacturing the oral thin film (OTF), in step (f), the substrate includes polyester film.

In specific embodiments, with the method of manufacturing the oral thin film (OTF), in step (f), the solvent casting is carried out at an elevated temperature.

In specific embodiments, with the method of manufacturing the oral thin film (OTF), in step (f), the solvent casting is carried out at temperature above about 100° F.

In specific embodiments, with the method of manufacturing the oral thin film (OTF), in step (f), the solvent casting is carried out at temperature above about 150° F.

In specific embodiments, with the method of manufacturing the oral thin film (OTF), in step (f), the solvent casting is carried out at temperature above about 200° F.

In specific embodiments, with the method of manufacturing the oral thin film (OTF), in step (f), the solvent casting is carried out at temperature above about 225° F.

In specific embodiments, with the method of manufacturing the oral thin film (OTF), in step (f), the solvent casting is carried out at temperature up to about 250° F.

In specific embodiments, with the method of orally administering the composition to a human, the composition is a composition as described herein.

In specific embodiments, with the method of orally administering the composition to a human, the composition is a unit dosage form as described herein.

In specific embodiments, with the method of orally administering the composition to a human, the composition is an oral thin film (OTF) as described herein.

In specific embodiments, with the method of orally administering the composition to a human, the composition is administered to the human to treat a condition ameliorated by any one or more of substances (i)-(v): (i) N-acetyl-5-methoxy tryptamine (melatonin), (ii) (–)-β-caryophyllene (caryophyllene), (iii) 4-aminobutanoic acid (GABA), (iv) L-γ-glutamylethylamide (L-theanine), and (v) pyridoxine (vitamin B6).

In specific embodiments, with the method of orally administering the composition to a human, the composition is administered to the human to treat a condition ameliorated by the combination of substances (i)-(v): (i) N-acetyl-5-methoxy tryptamine (melatonin), (ii) (–)-β-caryophyllene (caryophyllene), (iii) 4-aminobutanoic acid (GABA), (iv) L-γ-glutamylethylamide (L-theanine), and (v) pyridoxine (vitamin B6).

In specific embodiments, with the method of orally administering the composition to a human, the condition is a sleeping disorder (somnipathy).

In specific embodiments, with the method of orally administering the composition to a human, the condition is dyssomnias.

In specific embodiments, with the method of orally administering the composition to a human, the condition is insomnia.

In specific embodiments, with the method of orally administering the composition to a human, the condition is a sleeping disorder (somnipathy) characterized by at least one of: (i) difficulty getting to sleep, (ii) difficulty remaining asleep, (iii) poor sleep quality, (iv) decreasing sleepiness upon awakening, (v) only non-REM sleep, and (vi) preventing early awakenings.

In specific embodiments, with the method of orally administering the composition to a human, the condition is a sleeping disorder (somnipathy) characterized by the combination of: (i) difficulty getting to sleep, (ii) difficulty remaining asleep, (iii) poor sleep quality, (iv) decreasing sleepiness upon awakening, (v) only non-REM sleep, and (vi) preventing early awakenings.

In specific embodiments, with the method of orally administering the composition to a human, the method is a method of at least one of: (i) decreasing sleep onset latency, (ii) increasing total time slept, (iii) increasing overall sleep quality, (iv) decreasing sleepiness upon awakening, (v) promoting a deep sleep, (vi) promoting REM sleep, and (vii) preventing early awakenings.

In specific embodiments, with the method of orally administering the composition to a human, the method is a combination of: (i) decreasing sleep onset latency, (ii) increasing total time slept, (iii) increasing overall sleep quality, (iv) decreasing sleepiness upon awakening, (v) promoting a deep sleep, (vi) promoting REM sleep, and (vii) preventing early awakenings.

In specific embodiments, with the method of orally administering the composition to a human, an increase in the amount of REM sleep is obtained thereafter.

In specific embodiments, with the method of orally administering the composition to a human, at least about 30 minutes of REM sleep is obtained thereafter.

In specific embodiments, with the method of orally administering the composition to a human, at least about 45 minutes of REM sleep is obtained thereafter.

In specific embodiments, with the method of orally administering the composition to a human, at least about 60 minutes of REM sleep is obtained thereafter.

In specific embodiments, with the method of orally administering the composition to a human, at least about 75 minutes of REM sleep is obtained thereafter.

In specific embodiments, with the method of orally administering the composition to a human, at least about 90 minutes of REM sleep is obtained thereafter.

In specific embodiments, with the method of orally administering the composition to a human, about 45-110 minutes of REM sleep is obtained thereafter.

In specific embodiments, with the method of orally administering the composition to a human, about 60-100 minutes of REM sleep is obtained thereafter.

In specific embodiments, with the method of orally administering the composition to a human, an increase in the total time slept is obtained thereafter.

In specific embodiments, with the method of orally administering the composition to a human, at least about 6 hours of total time slept is obtained thereafter.

In specific embodiments, with the method of orally administering the composition to a human, at least about 6.5 hours of total time slept is obtained thereafter.

In specific embodiments, with the method of orally administering the composition to a human, at least about 7 hours of total time slept is obtained thereafter.

In specific embodiments, with the method of orally administering the composition to a human, at least about 7.5 hours of total time slept is obtained thereafter.

In specific embodiments, with the method of orally administering the composition to a human, at least about 8 hours of total time slept is obtained thereafter.

In specific embodiments, with the method of orally administering the composition to a human, at least about 8.5 hours of total time slept is obtained thereafter.

In specific embodiments, with the method of orally administering the composition to a human, the method is a short-term treatment of insomnia characterized by difficulties with sleep initiation.

In specific embodiments, with the method of orally administering the composition to a human, the method is a short-term treatment of insomnia characterized by difficulties with sleep initiation and excessive sleepiness upon awakening.

In specific embodiments, with the method of orally administering the composition to a human, the orally administering is carried out up to about 60 minutes prior to bedtime.

In specific embodiments, with the method of orally administering the composition to a human, the orally administering is carried out up to about 30 minutes prior to bedtime.

In specific embodiments, with the method of orally administering the composition to a human, the orally administering is carried out up to about 15 minutes prior to bedtime.

In specific embodiments, with the method of orally administering the composition to a human, the composition is in the form of an oral thin film (OTF), and 1-2 of the OTFs are administered up to about 60 minutes prior to bedtime.

In specific embodiments, with the method of orally administering the composition to a human, the composition is in the form of an oral thin film (OTF), and 1-2 of the OTFs are administered up to about 30 minutes prior to bedtime.

In specific embodiments, with the method of orally administering the composition to a human, the composition is in the form of an oral thin film (OTF), and 1-2 of the OTFs are administered up to about 15 minutes prior to bedtime.

In specific embodiments, with the method of orally administering the composition to a human, the composition is in the form of an oral thin film (OTF), and 1-2 of the OTFs are administered up to about 10 minutes prior to bedtime.

In specific embodiments, with the method of orally administering the composition to a human, the composition is in the form of an oral thin film (OTF), and 1-2 of the OTFs are administered about 10-15 minutes prior to bedtime.

In specific embodiments, with the method of orally administering the composition to a human, each of substances (i)-(v): (i) N-acetyl-5-methoxy tryptamine (melatonin), (ii) (−)-β-caryophyllene (caryophyllene), (iii) 4-aminobutanoic acid (GABA), (iv) L-γ-glutamylethylamide (L-theanine), and (v) pyridoxine (vitamin B6), is delivered sublingually.

In specific embodiments, with the method of orally administering the composition to a human, each of substances (i)-(v): (i) N-acetyl-5-methoxy tryptamine (melatonin), (ii) (−)-β-caryophyllene (caryophyllene), (iii) 4-aminobutanoic acid (GABA), (iv) L-γ-glutamylethylamide (L-theanine), and (v) pyridoxine (vitamin B6), is delivered buccally.

In specific embodiments, with the method of orally administering the composition to a human, each of substances (i)-(v): (i) N-acetyl-5-methoxy tryptamine (melatonin), (ii) (−)-β-caryophyllene (caryophyllene), (iii) 4-aminobutanoic acid (GABA), (iv) L-γ-glutamylethylamide (L-theanine), and (v) pyridoxine (vitamin B6), is delivered transmucosally.

In specific embodiments, with the method of orally administering the composition to a human, the composition is formulated as an oral thin film (OTF) that dissolves in the mouth within about 120 seconds after orally administering.

In specific embodiments, with the method of orally administering the composition to a human, the composition is formulated as an oral thin film (OTF) that dissolves in the mouth within about 60 seconds after orally administering.

In specific embodiments, with the method of orally administering the composition to a human, the composition is formulated as an oral thin film (OTF) that dissolves in the mouth within about 45 seconds after orally administering.

Enumerated Embodiments

Specific enumerated embodiments [1] to [57] provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

[1.] The present invention provides for a composition that includes:
(i) N-acetyl-5-methoxy tryptamine (melatonin),
(ii) (−)-β-caryophyllene (caryophyllene),
(iii) 4-aminobutanoic acid (GABA),
(iv) L-γ-glutamylethylamide (L-theanine),
(v) pyridoxine (vitamin $B_6$),
(vi) at least one of a binder, thickening agent, and gelling agent,
(vii) plasticizer,
(viii) lipid,
(iv) optionally a flavoring agent, and
(v) optionally a sweetener.

[2.] The present invention provides for the composition of the above embodiment, which is in the form of an oral thin film (OTF).

[3.] The present invention provides for the composition of any one of the above embodiments, which is in the form of an oral thin film (OTF) having a mass of about 110-130 mg.

[4.] The present invention provides for the composition of any one of the above embodiments, which is in the form of an oral thin film (OTF) having the following dimensions: about 44 mm x about 22 mm x about 0.12 mm.

[5.] The present invention provides for the composition of any one of the above embodiments, wherein the melatonin is present in about 1 wt. % to about 5 wt. %.

[6.] The present invention provides for the composition of any one of the above embodiments, formulated as a unit dosage form having a mass of about 110-130 mg and wherein the melatonin is present in about 1.35 mg to about 5.0 mg.

[7.] The present invention provides for the composition of any one of the above embodiments, wherein the caryophyllene is present in about 10 wt. % to about 25 wt. %.

[8.] The present invention provides for the composition of any one of the above embodiments, formulated as a unit dosage form having a mass of about 110-130 mg and wherein the caryophyllene is present in about 15 mg to about 25 mg.

[9.] The present invention provides for the composition of any one of the above embodiments, wherein the GABA is present in about 3 wt. % to about 15 wt. %.

[10.] The present invention provides for the composition of anyone of the above embodiments, formulated as a unit dosage form having a mass of about 110-130 mg and wherein the GABA is present in about 5 mg to about 15 mg.

[11.] The present invention provides for the composition of anyone of the above embodiments, wherein the L-theanine is present in about 3 wt. % to about 20 wt. %.

[12.] The present invention provides for the composition of anyone of the above embodiments, formulated as a unit dosage form having a mass of about 110-130 mg and wherein the L-theanine is present in about 5 mg to about 20 mg.

[13.] The present invention provides for the composition of anyone of the above embodiments, wherein the vitamin $B_6$ is present in about 1.5 wt. % to about 5.5 wt. %.

[14.] The present invention provides for the composition of anyone of the above embodiments, formulated as a unit dosage form having a mass of about 110-130 mg and wherein the vitamin $B_6$ is present in about 2 mg to about 6 mg.

[15.] The present invention provides for the composition of anyone of the above embodiments, wherein the binder, thickening agent, and/or gelling agent is selected from the group consisting of pectin, carboxymethyl cellulose sodium, pullulan, carrageenan, hydroxypropyl methylcellulose, microcrystalline cellulose, xanthan gum, polyvinylpyrrolidone, and combinations thereof.

[16.] The present invention provides for the composition of anyone of the above embodiments, wherein at least one of the binder, thickening agent, and gelling agent is present in a total amount of about 10 wt. % to about 40 wt. %.

[17.] The present invention provides for the composition of anyone of the above embodiments, wherein the plasticizer includes at least one of glycerol, sorbitol, propylene glycol, and polyethlene glycol.

[18.] The present invention provides for the composition of anyone of the above embodiments, wherein the plasticizer is present in about 5 wt. % to about 40 wt. %.

[19.] The present invention provides for the composition of anyone of the above embodiments, wherein the lipid includes at least one of lecithin, hydroxylated lecithin, grapeseed oil, cocoa butter, shea butter, olive oil, almond oil, peanut oil, canola oil, sesame oil, hazelnut oil, and coconut oil.

[20.] The present invention provides for the composition of any one of the above embodiments, wherein the lipid is present in about 2 wt. % to about 15 wt. %.

[21.] The present invention provides for the composition of any one of the above embodiments, wherein the flavoring agent is present and includes a natural flavoring agent.

[22.] The present invention provides for the composition of any one of the above embodiments, wherein the flavoring agent is present and includes an artificial flavoring agent.

[23.] The present invention provides for the composition of any one of the above embodiments, wherein the sweetener is present and includes at least one of sucralose, acesulfame potassium, xylitol, ammonium glycyrrhizinate and *stevia*.

[24.] The present invention provides for an oral thin film (OTF) having a mass of about 110-130 mg, the OTF including:
(i) about 1.35 mg to about 5 mg N-acetyl-5-methoxy tryptamine (melatonin),
(ii) about 15 mg to about 25 mg (−)-β-caryophyllene (caryophyllene),
(iii) about 5 mg to about 15 mg 4-aminobutanoic acid (GABA),
(iv) about 5 mg to about 20 mg L-γ-glutamylethylamide (L-theanine),
(v) about 2 mg to about 6 mg pyridoxine (vitamin $B_6$),
(vi) about 10 mg to about 50 mg in the aggregate of at least one of a binder, thickening agent, and gelling agent,
(vii) about 5 mg to about 50 mg plasticizer,
(viii) about 2 mg to about 20 mg lipid,
(iv) about 2 to about 15 mg flavoring agent, and
(v) about 5 mg to about 20 mg sweetener.

[25.] The present invention provides for an oral thin film (OTF) having a mass of about 110-130 mg, the OTF including:
(i) about 1.5±0.5 mg N-acetyl-5-methoxy tryptamine (melatonin),
(ii) about 15±5 mg (−)-β-caryophyllene (caryophyllene),
(iii) about 7.5±3 mg 4-aminobutanoic acid (GABA),
(iv) about 12±6 mg L-γ-glutamylethylamide (L-theanine),
(v) about 3±2 mg pyridoxine (vitamin B6),
(vi) about 29±15 mg in the aggregate of at least one of binder, thickening agent, and gelling agent,
(vii) about 10±4 mg plasticizer,
(viii) about 2±1 mg lipid,
(ix) about 8±5 mg flavoring agent, and
(x) about 8±5 mg sweetener.

[26.] The present invention provides for an oral thin film (OTF) having a mass of about 110-130 mg, the OTF including:
(i) about 1.5 mg N-acetyl-5-methoxy tryptamine (melatonin),
(ii) about 15 mg (−)-β-caryophyllene (caryophyllene),
(iii) about 7.5 mg 4-aminobutanoic acid (GABA),
(iv) about 12 mg L-γ-glutamylethylamide (L-theanine),
(v) about 3.0 mg pyridoxine (vitamin B6),
(vi) about 29 mg of combination of pectin and microcrystalline cellulose,
(vii) about 10 mg glycerin,
(viii) about 2 mg soy lecithin,
(iv) about 8 mg flavoring agents, and
(x) about 8 mg of a combination of sucralose and acesulfame potassium.

[27.] The present invention provides for a method of manufacturing an oral thin film (OTF), the method including:
(a) contacting (−)-β-caryophyllene (caryophyllene), 4-aminobutanoic acid (GABA), and pyridoxine (vitamin $B_6$) to provide a first solution,
(b) contacting the first solution and lipids to provide a second solution,
(c) contacting the second solution and plasticizer to provide a third solution,
(d) contacting the third solution, N-acetyl-5-methoxy tryptamine (melatonin), and L-γ-glutamylethylamide (L-theanine) to provide a fourth solution,
(e) either (1) or (2):
(1) contacting the fourth solution and (i) sweetener, (ii) flavoring agent, (iii) combination of sweetener and flavoring agent, (iv) first sweetener and then flavoring agent, or (v) first flavoring agent and then sweetener, to form a fifth solution, and contacting the fifth solution and at least one of binder, thickening agent, and gelling agent, from order of lowest viscosity to highest viscosity, to provide a sixth solution,
(2) contacting the fourth solution and at least one of binder, thickening agent, and gelling agent from order of lowest viscosity to highest viscosity, to provide a sixth solution, and
(f) placing on a substrate and solvent casting the sixth solution.

[28.] The present invention provides for the method of embodiment [27], wherein in step (a), the contacting includes rapidly mixing or blending, at about 90-100° F., to provide a first solution that is a homogeneous suspension.
[29.] The present invention provides for the method of any one of embodiments [27]-[28], wherein in step (b), the contacting includes rapidly mixing or blending, at about 90-100° F., to provide a second solution that is a homogeneous suspension.
[30.] The present invention provides for the method of any one of embodiments [27]-[29], wherein in step (c), the contacting includes rapidly mixing or blending, at about 90-100° F., to provide a third solution that is a homogeneous suspension.
[31.] The present invention provides for the method of anyone of embodiments [27]-[30], wherein in step (d), the contacting includes rapidly mixing or blending, at about 90-100° F., to provide a fourth solution that is a homogeneous suspension.
[32.] The present invention provides for the method of anyone of embodiments [27]-[31], wherein in step (e)(1), the contacting includes rapidly mixing or blending, at about 90-100° F., to provide a fifth solution that is a homogeneous suspension.
[33.] The present invention provides for the method of any one of embodiments [27]-[32], wherein in step (e)(1), the contacting includes rapidly mixing or blending, at about 90-100° F., to provide a sixth solution that is a homogeneous suspension.
[34.] The present invention provides for the method of any one of embodiments [27]-[33], wherein in step (e)(2), the contacting includes rapidly mixing or blending, at about 90-100° F., to provide a sixth solution that is a homogeneous suspension.
[35.] The present invention provides for the method of any one of embodiments [27]-[34], wherein the substrate includes at least one of siliconized paper and polyester film.
[36.] The present invention provides for the method of any one of embodiments [27]-[35], wherein the solvent casting is carried out at an elevated temperature.
[37.] The present invention provides for the method of any one of embodiments [27]-[36], wherein the solvent casting is carried out at a temperature of up to about 250° F.
[38.] The present invention provides for the method of any one of embodiments [27]-[37], wherein the solvent casting is carried out at a temperature of about 225-250° F.
[39.] The present invention provides for a method including orally administering the composition of any one of embodiments [1]-[23] or the oral thin film (OTF) of any one of embodiments [24]-[26], to a human, to treat a condition ameliorated by any one or more of substances (i)-(v), in an amount and for a period of time effective to treat the condition.
[40.] The present invention provides for the method of embodiment [39], wherein the condition is a sleeping disorder (somnipathy).
[41.] The present invention provides for the method of embodiment [39], wherein the condition is dyssomnias.
[42.] The present invention provides for the method of embodiment [39], wherein the condition is insomnia.
[43.] The present invention provides for the method of embodiment [39], wherein the condition is a sleeping disorder (somnipathy) characterized by at least one of:
  (i) difficulty getting to sleep,
  (ii) difficulty remaining asleep,
  (iii) poor sleep quality,
  (iv) decreasing sleepiness upon awakening,
  (v) only non-REM sleep, and
  (vi) preventing early awakenings.
[44.] The present invention provides for the method of embodiment [39], wherein the condition is a sleeping disorder (somnipathy) characterized by each of:
  (i) difficulty getting to sleep,
  (ii) difficulty remaining asleep,
  (iii) poor sleep quality,
  (iv) decreasing sleepiness upon awakening,
  (v) only non-REM sleep, and
  (vi) preventing early awakenings.
[45.] The present invention provides for the method of any one of embodiments [39]-[44], which is a method of at least one of:
  (i) decreasing sleep onset latency,
  (ii) increasing total time slept,
  (iii) increasing overall sleep quality,
  (iv) decreasing sleepiness upon awakening,
  (v) promoting a deep sleep,
  (vi) promoting REM sleep, and
  (vii) preventing early awakenings.
[46.] The present invention provides for the method of any one of embodiments [39]-[44], which is a method of each of:
  (i) decreasing sleep onset latency,
  (ii) increasing total time slept,
  (iii) increasing overall sleep quality,
  (iv) decreasing sleepiness upon awakening,
  (v) promoting a deep sleep,
  (vi) promoting REM sleep, and
  (vii) preventing early awakenings.
[47.] The present invention provides for the method of any one of embodiments [39]-[46], which is a short-term treatment of insomnia characterized by difficulties with sleep initiation.
[48.] The present invention provides for the method of any one of embodiments [39]-[47], which is a short-term treatment of insomnia characterized by difficulties with sleep initiation and excessive sleepiness upon awakening.
[49.] The present invention provides for the method of any one of embodiments [39]-[48], wherein the orally administering is carried out up to about 30 minutes prior to bedtime.
[50.] The present invention provides for the method of any one of embodiments [39]-[48], wherein the composition is in the form of an oral thin film (OTF), and 1-2 of the OTFs are administered up to about 30 minutes prior to bedtime.
[51.] The present invention provides for the method of anyone of embodiments [39]-[50], wherein each of substances (i)-(v) is delivered sublingually.
[52.] The present invention provides for the method of any one of embodiments [39]-[50], wherein each of substances (i)-(v) is delivered buccally.
[53.] The present invention provides for the method of any one of embodiments [39]-[50], wherein each of substances (i)-(v) is delivered transmucosally.
[54.] The present invention provides for the method of any one of embodiments [39]-[53], wherein the composition is formulated as a unit dosage form.
[55.] The present invention provides for the method of any one of embodiments [39]-[54], wherein the composition is formulated as an oral thin film (OTF).
[56.] The present invention provides for the method of any one of embodiments [39]-[55], wherein the composition is formulated as an oral thin film (OTF) that dissolves in the mouth within about 30 seconds after orally administering to the human subject.
[57.] The present invention provides for a method including orally administering the composition of any one of embodiments [1]-[23] or the oral thin film (OTF) of any one of embodiments [24]-[26], to a human, to treat a condition ameliorated by the combination of substances (i)-(v), in an amount and for a period of time effective to treat the condition.

Example

Stability and Testing 1 strip samples were manufactured as described herein (Product Lot #05142018-2) and tested, with the results shown below. The storage conditions were 55 to 85° F. (12 to 29° C.) and protected from moisture, heat and humidity.

| TEST | SPECIFICATION | METHOD | RESULTS |
|---|---|---|---|
| Color | Light yellow | IM-204 | Pass |
| Odor | Mint | IM-204 | Pass |
| Appearance | No clumping/breaking of strips | IM-204 | Pass |
| Melatonin | ≥1.35 mg | MQLTM-0491 | 1.72 mg |
| GABA | ≥6.75 mg | MQLTM-0222 | 8.15 mg |
| L-theanine | ≥10.8 mg | MQLTM-0198 | 14.3 mg |
| Vitamin B6 | ≥2.7 mg | MQLTM-0153 | 3.2 mg |
| Total Plate Count | <1,000 cfu/g | USP61 | <10 cfu/g |
| Yeast/Mold | <100 cfu/g | USP61 | <10 cfu/g |
| Coliforms | <10 cfu/g | USP 62 | <10 cfu/g |
| E. Coli | Absent | USP 62 | Absent |
| Pseudomonas | Absent | USP 62 | Absent |
| S. aureus | Absent | USP 62 | Absent |
| Salmonella/Shigella | Absent | USP 62 | Absent |

The invention claimed is:

1. A method of improving sleep in a human subject, the method comprising orally administering to the human subject in need thereof an oral thin film having a mass of about 110-130 mg, the oral thin film comprising:
   (i) 1.5±0.5 mg Nacetyl-5-methoxy tryptamine (melatonin),
   (ii) 15±5 mg (−)-β-caryophyliene (caryophyllene),
   (iii) 7.5±3 mg 4-aminobutanoic acid (GABA),
   (iv) 12±6 mg L-γ-glutamylethylamide (L-theanine),
   (v) 3±2 mg pyridoxine (vitamin B6),
   (vi) 29±15 mg in the aggregate of at least one of binder, thickening agent, and gelling agent, comprising pectin and microcrystalline cellulose,
   (vii) 10±4 mg plasticizer comprising glycerin,
   (viii) 2±1 mg lipid comprising lecithin (soy) and deodorized cocoa butt,
   (ix) 8±5 mg flavoring agent comprising natural flavors, and
   (x) 8±5 mg sweetener comprising sucralose and acesulfame potassium.

2. The method of claim 1, wherein the method of improving the sleep in the subject comprises at least one of improving the quality of sleep and increasing the length of time of sleep.

3. The method of claim 1, wherein the method of improving the sleep in the subject comprises treating at least one of a sleeping disorder (somnipathy), dyssomnias, and insomnia.

4. The method of claim 1, wherein the method of improving the sleep in the subject comprises treating a sleeping disorder (somnipathy) characterized by at least one of:
   (i) difficulty getting to sleep,
   (ii) difficulty remaining asleep,
   (iii) sleepiness upon awakening,
   (iv) significant amount of non-REM sleep, and
   (i) early awakenings.

5. The method of claim 1, wherein the method of improving the sleep in the subject comprises at least one of:
   (i) decreasing sleep onset latency,
   (ii) increasing total time slept,
   (iii) decreasing sleepiness upon awakening,
   (iv) promoting a deep sleep,
   (v) promoting REM sleep, and
   (vi) preventing early awakenings.

6. The method of claim 1, wherein the oral film is placed on the tongue of the subject.

7. The method of claim 1, wherein the oral film is orally administered up to about 30 minutes prior to bedtime.

8. The method of claim 1, wherein 1-2 of the oral films are orally administered up to about 30 minutes prior to bedtime.

9. The method of claim 1, wherein substances (i)-(v) are delivered enterally.

10. The method of claim 1, wherein substances (i)-(v) are delivered sublingually.

11. The method of claim 1, wherein substances (i)-(v) are delivered buccally.

12. The method of claim 1, wherein substances (i)-(v) are delivered transmucosally.

13. The method of claim 1, wherein the oral thin film has a thickness of from about 0.1 mils to about 30 mils and wherein the oral thin film completely dissolves in the oral cavity within about 90 seconds after orally administering to the human subject.

14. The method of claim 1, wherein the oral thin film has a thickness of from about 0.1 mils to about 30 mils and wherein the oral thin film completely dissolves in the oral cavity within about 60 seconds after orally administering to the human subject.

15. The method of claim 1, wherein 1-2 of the oral thin film (OTFs) are administered up to about 15 minutes prior to bedtime.

16. The method of claim 1, wherein oral thin film (OTF) that dissolves in the mouth within about 120 seconds after orally administering to the human subject.

17. The method of claim 1, wherein the oral thin film (OM has the following dimensions: 44±3 mm x 22±1 mm x 0.1.2±0.01 mm.

18. The method of claim 1, wherein the oral thin film (OTF) has the following dimensions: 44±6 mm x 22±3 mm x 0.12±0.02 mm.

19. The method of claim 1, which is a short-term treatment of insomnia characterized by difficulties with sleep initiation and excessive sleepiness upon awakening.

20. The method of claim 1, wherein 1-2 of the oral thin film (OTFs) are administered up to about 30 minutes prior to bedtime.

21. The method of claim 1, wherein the oral thin film (OTF) dissolves in the mouth within about 30 seconds after orally administering to the human subject.

22. The method of claim 1, wherein the oral thin film further comprises water.

* * * * *